(12) United States Patent
Wells et al.

(10) Patent No.: US 7,183,063 B2
(45) Date of Patent: Feb. 27, 2007

(54) CHEMOKINE RECEPTOR ABLE TO BIND TO MCP-1, MIP-1 α AND/OR RANTES AND ITS USES

(75) Inventors: Timothy N. C. Wells, Geneva (CH); Christine A. Power, Geneva (CH)

(73) Assignee: Glaxo Group Limited, Greenford (GB)

( * ) Notice: Subject to any disclaimer, the term of this patent is extended or adjusted under 35 U.S.C. 154(b) by 322 days.

(21) Appl. No.: 10/120,394

(22) Filed: Apr. 12, 2002

(65) Prior Publication Data

US 2002/0160015 A1 Oct. 31, 2002

Related U.S. Application Data

(62) Division of application No. 09/614,256, filed on Jul. 12, 2000, now abandoned, which is a continuation of application No. 08/875,573, filed as application No. PCT/GB96/00143 on Jan. 24, 1996, now Pat. No. 6,150,132.

(30) Foreign Application Priority Data

Jan. 27, 1995 (GB) ............................................ 9501683

(51) Int. Cl.
*G01N 33/53* (2006.01)
*G01N 33/567* (2006.01)

(52) U.S. Cl. .................. 435/7.21; 435/7.1; 435/7.2; 436/501

(58) Field of Classification Search .................. 435/7.1, 435/7.2, 7.21; 436/501
See application file for complete search history.

(56) References Cited

U.S. PATENT DOCUMENTS

| 6,132,987 A | * | 10/2000 | Charo et al. ............... 435/69.1 |
| 6,150,132 A | | 11/2000 | Wells et al. |
| 6,919,432 B2 | | 7/2005 | Wells et al. |
| 2005/0014695 A1 | | 1/2005 | Wells et al. |

FOREIGN PATENT DOCUMENTS

| EP | 0805859 B1 | 4/2005 |
| WO | WO 92/20372 | 11/1992 |
| WO | WO 94/07521 | 4/1994 |
| WO | WO 94/11504 | 5/1994 |
| WO | WO 94/21277 | 9/1994 |
| WO | WO 94/29348 | 12/1994 |

OTHER PUBLICATIONS

Bischoff et al (1993) "RANTES and related chemokines activate human basophil granulocyles through different G protein–coupled receptors" Eur J Immunol 23:761–767.
Charo et al. (1994) "Molecular cloning and functional expression of two monocyte chemoattractant protein 1 receptors reveals alternative splicing of the carboxyl–terminal tails" Proc Natl Acad Sci USA 91:2752–2756.
Chvatchko et al (2000) "A key role for CC chemokine receptor 4 in lipopolysaccharide–induced endotoxic shock" J Exp Med 191:1755–1763.
Gao et al (1993) "Structure and functional expression of the human macrophage inflammatory protein 1 alpha/RANTES receptor" J Exp Med 177:1421–1427.
Gao et al (1994) "Human cytomegalovirus open reading frame US28 encodes a functional beta chemokine receptor" J Biol Chem 269:28539–28542.
Gieorge et al (1988) "Macromolecular sequencing and synthesis" Alan R. Liss. pp 127–149.
Graham et al (1990) "Identification and characterization of an inhibitor of haemopoietic stem cell proliferation" Nature 344:442–444.
Kawasaki et al (2001) "Intervention of thymus and activation–regulated chemokine attenuates the development of allergic airway inflammation and hyperresponsive in Mice" J Immunol 166:2055–2062.
Libert et al (1989) "Selective amplification and cloning of four new members of the G protein–coupled receptor family" Science 244:569–572.
Neote et al (1993) "Molecular cloning, functional characteristics of a CC chemokine receptor" Cell 72:415–425.
Panina–Bordignon et al (2001) "The C–C chemokine receptors CCR4 and CCR8 identify airway T cells of allergen–challenged atopic asthmatics" J Clin Invest 107:1357–1364.
Power et al (1995) "Molecular cloning and functional expression of a novel CC chemokine receptor cDNA from a human basophilic cell line" J Biol Chem 270:19495–19500.
Yamagami et al (1994) "cDNA cloning and functional expression of a human monocyte chemoattractant protein 1 receptor" Biochem Biophys Res Comm 202:1156–1162.
Hoogewerf et al. "Molecular cloning of murine CC CKR–4 and high affinity binding of chemokines to murine and human CC CKR–4" Biochem.Biophys. Res. Comm. 218:337–343 (1996).
Horuk et al. "Molecular properties of the chemokine receptor family" TiPS 15:159–165 (1994).
Imai et al. "Molecular cloning of a novel T cell–directed CC chemokine expressed in thymus by signal sequence trap using Epstein–Barr virus vector" J. Biol. Chem. 271:21514–21521 (1996).

(Continued)

*Primary Examiner*—John Ulm
(74) *Attorney, Agent, or Firm*—Nixon & Vanderhye P.C.

(57) ABSTRACT

A chemokine receptor binds to MCP-1, MIP-1α and/or RANTES. It can be used in screening for agents which act as antagonists to MCP-1, MIP-1α and/or RANTES. Such agents may be useful in treating various disorders, including allergies, atheromas and diseases mediated by viruses. They may also be useful in preventing graft rejection and in protecting stem cells from potentially damaging effects of chemotherapy.

16 Claims, 7 Drawing Sheets

OTHER PUBLICATIONS

Imai et al. "The T cell–directed CC chemokine TARC is a highly specific biological ligand for CC chemokine receptor 4" J. Biol. Chem. 272:15036–15042 (1997).

Imai et al. "Macrophage–derived chemokine is a functional ligand for the CC chemokine receptor 4" J. Biol. Chem. 273:1764–1768 (1998).

Jones et al. "Replacing the complementarity–determining regions in a human antibody with those from a mouse" Nature 321:522–525 (1986).

Kelvin et al. "Chemokines and serpentines: The molecular biology of chemokine receptors" J. Leukocyte Biol. 54:604–612 (1993).

Riechmann et al. "Reshaping human antibodies for therapy" Nature 332:323–327 (1988).

Reiss et al. "CC chemokine receptor (CCR)4 and the CCR10 ligand cutaneous T cell–attracting chemokine (CTACK) in lymphocyte trafficking to inflamed skin" J. Exp. Med. 194:1541–1547 (2001).

* cited by examiner

FIG. 1 cDNA sequence and deduced amino acid sequence of clone TM(2-7)5.5

```
  1 GGTATCTGGCGATAGTGCACGCGGTGTTTTCCTTGAGGGCAAGGACCTTGACTTATGGGG  60
    Y  L  A  I  V  H  A  V  F  S  L  R  A  R  T  L  T  Y  G  V
 61 TCATCACCAGTTTGGCTACATGGTCAGTGGCTGTGTTCGCCTCCCTTCCTGGCTTTCTGT 120
    I  T  S  L  A  T  W  S  V  A  V  F  A  S  L  P  G  F  L  F
121 TCAGCACTTGTTATACTGAGCGCAACCATACCTACTGCAAAACCAAGTACTCTCTCAACT 180
    S  T  C  Y  T  E  R  N  H  T  Y  C  K  T  K  Y  S  L  N  S
181 CCACGACGTGGAAGGTTCTCAGCTCCCTGGAAANCAACATTCTCGGATTGGTGATCCCCT 240
    T  T  W  K  V  L  S  S  L  E  X  N  I  L  G  L  V  I  P  L
241 TAGGGATCATGCTGTTTTGCTACTCCATGATCATCAGGACCTTGCAGCATTGTAAAAATG 300
    G  I  M  L  F  C  Y  S  M  I  I  R  T  L  Q  H  C  K  N  E
301 AGAAGAAGAACAAGGCGGTGAAGATGATCTTTGCCGTGGTGGTCCTCTTCCTTGGGTTCT 360
    K  K  N  K  A  V  K  M  I  F  A  V  V  V  L  F  L  G  F  W
361 GGACACCTTACAACATAGTGCTCTTCCTAGAGACCCTGGTGGAGCTAGAAGTCCTTCAGG 420
    T  P  Y  N  I  V  L  F  L  E  T  L  V  E  L  E  V  L  Q  D
421 ACTGCACCTTTGAAAGATACTTGGACTATGCCAGCCAGGCCACAGAAACTCTGGCTTTTG 480
    C  T  F  E  R  Y  L  D  Y  A  S  Q  A  T  E  T  L  A  F  V
481 TTCACTGCTGCCTCAATCCCCTCCTCTACGCCGT 514
    G  C  C  L  N  P  L  L  Y  A
```

FIG. 2

Oligonucleotide primers used to determine the full sequence of E1-C19

| | | |
|---|---|---|
| K5-5AS | 5' AGA GTA CTT GGT TTT GCA GTA G | (ANTISENSE) |
| K5-5AS2 | 5' GCA GCA GTG AAC AAA AGC CAG | (ANTISENSE) |
| K5-5A | 5' CAT AGT GCT CTT CCT AGA GAC | (SENSE) |
| K5-5B | 5' GGT TGA GCA GGT ACA CAT CAG | (ANTISENSE) |
| K5-5C | 5' CAA TAC TGT GGG CTC CTC C | (SENSE) |
| K5-5D | 5' GCT CAG GTC CAT GAC TG | (SENSE) |
| K5-5E | 5' CTC ATG AGC ATT GAT AG | (SENSE) |
| K5-5F | 5' CTG AGC GCA ACC ATA CC | (SENSE) |
| K5-5G | 5' GCT AGA AGT CCT TCA GG | (SENSE) |
| K5-5H | 5' GGA TCA TGA TCT TCA TG | (SENSE) |
| K5-5FLA | 5' AAA TGA AAC CCC ACG GAT ATA GCAG | (SENSE) |
| K5-5FLB | 5' TCC TAC AGA GCA TCA TGA AGA TC | (ANTISENSE) |

FIG. 3A cDNA sequence and deduced amino acid sequence of K5.5

```
  1 CGGGGGTTTTCATCTTCTTCCCCTTCTTTTCTTCCCCTTCTTCTTTCCTTCCTCCCTCCC   60

61 TCTCTCATTTCCCTTCTCCTTCTCCCTCAGTCTCCACATTCAACATTGACAAGTCCATTC  120

121 AGAAAAGCAAGCTGCTTCTGGTTGGGCCCAGACCTGCCTTGAGGAGCCTGTAGAGTTAAA  180

181 AAATGAACCCCACGGATATAGCAGATACCACCCTCGATGAAAGCATATACAGCAATTACT  240
      M  N  P  T  D  I  A  D  T  T  L  D  E  S  I  Y  S  N  Y  Y
241 ATCTGTATGAAAGTATCCCCAAGCCTTGCACCAAAGAAGGCATCAAGGCATTTGGGGAGC  300
      L  Y  E  S  I  P  K  P  C  T  K  E  G  I  K  A  F  G  E  L
301 TCTTCCTGCCCCCACTGTATTCCTTGGTTTTTGTATTTGGTCTGCTTGGAAATTCTGTGG  360
      F  L  P  P  L  Y  S  L  V  F  V  F  G  L  L  G  N  S  V  V
361 TGGTTCTGGTCCTGTTCAAATACAAGCGGCTCAGGTCCATGACTGATGTGTACCTGCTCA  420
      F  L  P  P  L  Y  S  L  V  F  V  F  G  L  L  G  N  S  V  V
421 ACCTTGCCATCTCGGATCTGCTCTTCGTGTTTTCCCTCCCTTTTGGGGCTACTATGCAG  480
      L  A  I  S  D  L  L  F  V  F  S  L  P  F  W  G  Y  Y  A  A
481 CAGACCAGTGGGTTTTTGGGCTAGGTCTGTGCAAGATGATTTCCTGGATGTACTTGGTGG  540
      D  Q  W  V  F  G  L  G  L  C  K  M  I  S  W  M  Y  L  V  G
541 GCTTTTACAGTGGCATATTCTTTGTCATGCTCATGAGCATTGATAGATACCTGGCGATAG  600
      F  Y  S  G  I  F  F  V  M  L  M  S  I  D  R  Y  L  A  I  V
601 TGCACGCGGTGTTTTCCTTGAGGGCAAGGACCTTGACTTATGGGGTCATCACCAGTTTGG  660
      H  A  V  F  S  L  R  A  R  T  L  T  Y  G  V  I  T  S  L  A
661 CTACATGGTCAGTGGCTGTGTTCGCCTCCCTTCCTGGCTTTCTGTTCAGCACTTGTTATA  720
      T  W  S  V  A  V  F  A  S  L  P  G  F  L  F  S  T  C  Y  T
721 CTGAGCGCAACCATACCTACTGCAAAACCAAGTACTCTCTCAACTCCACGACGTGGAAGG  780
      E  R  N  H  T  Y  C  K  T  K  Y  S  L  N  S  T  T  W  K  V
781 TTCTCAGCTCCCTGGAAATCAACATTCTCGGATTGGTGATCCCCTTAGGGATCATGCTGT  840
      L  S  S  L  E  I  N  I  L  G  L  V  I  P  L  G  I  M  L  F
```

```
 781 TTCTCAGCTCCCTGGAAATCAACATTCTCGGATTGGTGATCCCCTTAGGGATCATGCTGT  840
      L  S  S  L  E  I  N  I  L  G  L  V  I  P  L  G  I  M  L  F
 841 TTTGCTACTCCATGATCATCAGGACCTTGCAGCATTGTAAAAATGAGAAGAAGAACAAGG  900
      C  Y  S  M  I  I  R  T  L  Q  H  C  K  N  E  K  K  N  K  A
 901 CGGTGAAGATGATCTTTGCCGTGGTGGTCCTCTTCCTTGGGTTCTGGACACCTTACAACA  960
      V  K  M  I  F  A  V  V  V  L  F  L  G  F  W  T  P  Y  N  I
 961 TAGTGCTCTTCCTAGAGACCCTGGTGGAGCTAGAAGTCCTTCAGGACTGCACCTTTGAAA 1020
      V  L  F  L  E  T  L  V  E  L  E  V  L  Q  D  C  T  F  E  R
1021 GATACTTGGACTATGCCATCCAGGCCACAGAAACTCTGGCTTTTGTTCACTGCTGCCTTA 1080
      Y  L  D  Y  A  I  Q  A  T  E  T  L  A  F  V  H  C  C  L  N
1081 ATCCCATCATCTACTTTTTTCTGGGGGAGAAATTTCGCAAGTACATCCTACAGCTCTTCA 1140
      P  I  I  Y  F  F  L  G  E  K  F  R  K  Y  I  L  Q  L  F  K
1141 AAACCTGCAGGGGCCTTTTTGTGCTCTGCCAATACTGTGGGCTCCTCCAAATTTACTCTG 1200
      T  C  R  G  L  F  V  L  C  Q  Y  C  G  L  L  Q  I  Y  S  A
1201 CTGACACCCCCAGCTCATCTTACACGCAGTCCACCATGGATCATGATCTCCATGATGCTC 1260
      D  T  P  S  S  Y  T  Q  S  T  M  D  H  D  L  H  D  A  L
1261 TGTAGAAAAATGAAATGGTGAAATGCAGAGTCAATGAACTTTTCCACATTCAGAGCTTAC 1320
      *
1321 TTTAAAATTGGTATTTTTAGGTAAGAGATCCCTGAGCCAGTGGTCAGGAGGAAAGGCTTA 1380

1381 CACCCACAGGTGGGAAAGACAGGTTCTCATCCCTGCAGGNAGGTTTTTCTTCTCCCCACT 1440

1441 TAGANAAAGTNCCAGGCCTGGAAGGGGTCCAACCCNGGGTTGAGGATCCTTCCCCCAAAC 1500

1501 CCAGGGTTTGGCCTGGAGGATTAATNCAAAANNTTTNTTGAAACTCTTGAANANGTTGNG 1560

1561 NTAAGTTTNGGGGGGTTNTTTTGAAGGNAAGTTTTTCCCTTCTTNCC 1607
```

Northern blot analysis of K5.5 expression in peripheral tissues

| TISSUE | K5.5 |
|---|---|
| HEART | - |
| BRAIN | - |
| PLACENTA | - |
| LUNG | - |
| LIVER | - |
| SKELETAL MUSCLE | - |
| KIDNEY | - |
| PANCREAS | - |
| SPLEEN | ++ |
| THYMUS | +++ |
| PROSTATE | - |
| TESTIS | +/- |
| OVARY | - |
| SMALL INTESTINE | +/- |
| COLON | - |
| PERIPHERAL BLOOD LEUKOCYTES | +++ |

FIG. 5

Expression of K5.5 receptor mRNA peripheral blood T cell populations and some T cell lines.

| T CELL / T CELL LINES | K5.5 |
|---|---|
| T CELLS + IL-2 (4h) | ++ |
| T CELLS + IL-2 (12h) | ++ |
| T CELLS + IL-2 (24h) | ++ |
| T CELLS + IL-2 (48h) | ++ |
| T CELLS + IL-2 (72h) | ++ |
| T CELLS + IL-2 (7 DAYS) | ++ |
| T CELLS + PMA (2 DAYS) | ++ |
| JURKAT | + |
| MOLT-4 | +/- |
| T CELLS (UNSTIMULATED) | + |
| CD8 + T CELL CLONE | + |
| T8 CLONE | +++ |
| T8 + GH | +++ |
| T8 + GR | - |
| T8 + Giα | + |
| T4 CLONE | +++ |
| TT20 (IL2 STIMULATED) | ++ |
| CD45 RO | - |
| CD45 RO (STIMULATED) | - |
| CD45 RA | - |
| CD45 RA (STIMULATED) | - |
| HUT 78 | - |
| HUT 78 (STIMULATED) | - |

FIG. 6

Expression of K5.5 receptor mRNA in non-T leukocytes and cell lines

| NON-T CELL LEUKOCYTES / LINES | K5.5 |
|---|---|
| PERIPHERAL BLOOD B CELLS | + |
| B CELLS (ACTIVATED) | |
| RAJI | - |
| GCC (TONSIL) | - |
| GCC (ANTI CD40 MAb) | - |
| BL2 LINE | - |
| RPMI 8666 | - |
| KU812 | ++ |
| EOL-3 LINE | +/- |
| MACROPHAGES (ALVEOLAR) | - |
| MIXED LUNG LEUKOCYTES | +/- |
| MONOCYTES | - |
| HMC-1 LINE | - |

FIG. 7

Analysis of K5.5 receptor mRNA expression by RT-PCR in human cell lines and peripheral blood leukocyte populations

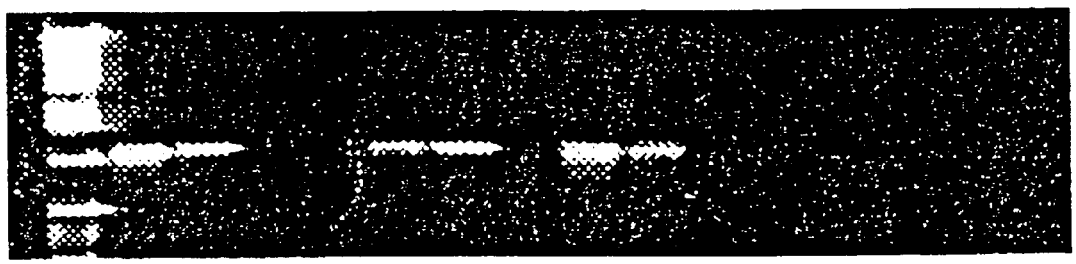

Current induced in voltage clamped oocytes on stimulation with different chemokine ligands (1μM) at 2 min intervals (results of individual oocytes tested are shown).

SEQUENCE LISTING (1) GENERAL INFORMATION:

(iii) NUMBER OF SEQUENCES: 20

(2) INFORMATION FOR SEQ ID NO: 1:

(i) SEQUENCE CHARACTERISTICS:
      (A) LENGTH: 8 amino acids
      (B) TYPE: amino acid

```
            (C) STRANDEDNESS: <Unknown>
            (D) TOPOLOGY: linear (ii) MOLECULE TYPE: peptide (xi) SEQUENCE DESCRIPTION: SEQ ID NO: 1:

Arg Tyr Leu Ala Ile Val His Ala
 1               5

(2) INFORMATION FOR SEQ ID NO: 2:

(i) SEQUENCE CHARACTERISTICS:
            (A) LENGTH: 9 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 2:

Cys Xaa Asn Pro Xaa Xaa Tyr Xaa Xaa
 1               5

(2) INFORMATION FOR SEQ ID NO: 3:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO: 3:

GNTAYYTNGC NATHGTNCAY GC                                              22

(2) INFORMATION FOR SEQ ID NO: 4:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(iv) ANTI-SENSE: YES (xi) SEQUENCE DESCRIPTION: SEQ ID NO: 4:

AMNRCRTTAN ADNANNGGRT TNANRC                                          26

(2) INFORMATION FOR SEQ ID NO: 5:

(i) SEQUENCE CHARACTERISTICS:
            (A) LENGTH: 514 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: CDS
            (B) LOCATION: 3..512

(xi) SEQUENCE DESCRIPTION: SEQ ID NO: 5:

GG TAT CTG GCG ATA GTG CAC GCG GTG TTT TCC TTG AGG GCA AGG ACC        47
   Tyr Leu Ala Ile Val His Ala Val Phe Ser Leu Arg Ala Arg Thr
```

```
                1               5                   10                  15
TTG ACT TAT GGG GTC ATC ACC AGT TTG GCT ACA TGG TCA GTG GCT GTG              95
Leu Thr Tyr Gly Val Ile Thr Ser Leu Ala Thr Trp Ser Val Ala Val
                        20                  25                  30

TTC GCC TCC CTT CCT GGC TTT CTG TTC AGC ACT TGT TAT ACT GAG CGC             143
Phe Ala Ser Leu Pro Gly Phe Leu Phe Ser Thr Cys Tyr Thr Glu Arg
                35                  40                  45

AAC CAT ACC TAC TGC AAA ACC AAG TAC TCT CTC AAC TCC ACG ACG TGG             191
Asn His Thr Tyr Cys Lys Thr Lys Tyr Ser Leu Asn Ser Thr Thr Trp
            50                  55                  60

AAG GTT CTC AGC TCC CTG GAA ANC AAC ATT CTC GGA TTG GTG ATC CCC             239
Lys Val Leu Ser Ser Leu Glu Xaa Asn Ile Leu Gly Leu Val Ile Pro
        65                  70                  75

TTA GGG ATC ATG CTG TTT TGC TAC TCC ATG ATC ATC AGG ACC TTG CAG             287
Leu Gly Ile Met Leu Phe Cys Tyr Ser Met Ile Ile Arg Thr Leu Gln
    80                  85                  90                  95

CAT TGT AAA AAT GAG AAG AAG AAC AAG GCG GTG AAG ATG ATC TTT GCC             335
His Cys Lys Asn Glu Lys Lys Asn Lys Ala Val Lys Met Ile Phe Ala
                        100                 105                 110

GTG GTG GTC CTC TTC CTT GGG TTC TGG ACA CCT TAC AAC ATA GTG CTC             383
Val Val Val Leu Phe Leu Gly Phe Trp Thr Pro Tyr Asn Ile Val Leu
                115                 120                 125

TTC CTA GAG ACC CTG GTG GAG CTA GAA GTC CTT CAG GAC TGC ACC TTT             431
Phe Leu Glu Thr Leu Val Glu Leu Glu Val Leu Gln Asp Cys Thr Phe
            130                 135                 140

GAA AGA TAC TTG GAC TAT GCC AGC CAG GCC ACA GAA ACT CTG GCT TTT             479
Glu Arg Tyr Leu Asp Tyr Ala Ser Gln Ala Thr Glu Thr Leu Ala Phe
        145                 150                 155

GTT CAC TGC TGC CTC AAT CCC CTC CTC TAC GCC GT                              514
Val His Cys Cys Leu Asn Pro Leu Leu Tyr Ala
160                 165                 170
```

(2) INFORMATION FOR SEQ ID NO: 6:

(i) SEQUENCE CHARACTERISTICS:
        (A) LENGTH: 170 amino acids
        (B) TYPE: amino acid
        (D) TOPOLOGY: linear (ii) MOLECULE TYPE: protein (xi) SEQUENCE DESCRIPTION: SEQ ID NO: 6:

```
Tyr Leu Ala Ile Val His Ala Val Phe Ser Leu Arg Ala Arg Thr Leu
 1               5                   10                  15

Thr Tyr Gly Val Ile Thr Ser Leu Ala Thr Trp Ser Val Ala Val Phe
                20                  25                  30

Ala Ser Leu Pro Gly Phe Leu Phe Ser Thr Cys Tyr Thr Glu Arg Asn
            35                  40                  45

His Thr Tyr Cys Lys Thr Lys Tyr Ser Leu Asn Ser Thr Thr Trp Lys
        50                  55                  60

Val Leu Ser Ser Leu Glu Xaa Asn Ile Leu Gly Leu Val Ile Pro Leu
 65                 70                  75                  80

Gly Ile Met Leu Phe Cys Tyr Ser Met Ile Ile Arg Thr Leu Gln His
                85                  90                  95

Cys Lys Asn Glu Lys Lys Asn Lys Ala Val Lys Met Ile Phe Ala Val
                100                 105                 110

Val Val Leu Phe Leu Gly Phe Trp Thr Pro Tyr Asn Ile Val Leu Phe
            115                 120                 125

Leu Glu Thr Leu Val Glu Leu Glu Val Leu Gln Asp Cys Thr Phe Glu
```

```
            130             135             140
Arg Tyr Leu Asp Tyr Ala Ser Gln Ala Thr Glu Thr Leu Ala Phe Val
145                 150                 155                 160

His Cys Cys Leu Asn Pro Leu Leu Tyr Ala
                165                 170
```

(2) INFORMATION FOR SEQ ID NO: 7:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(iv) ANTI-SENSE: YES (xi) SEQUENCE DESCRIPTION: SEQ ID NO: 7:

AGAGTACTTG GTTTTGCAGT AG                                22

(2) INFORMATION FOR SEQ ID NO: 8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(iv) ANTI-SENSE: YES (xi) SEQUENCE DESCRIPTION: SEQ ID NO: 8:

GCAGCAGTGA ACAAAAGCCA G                                 21

(2) INFORMATION FOR SEQ ID NO: 9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 9:

CATAGTGCTC TTCCTAGAGA C                                 21

(2) INFORMATION FOR SEQ ID NO: 10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(iv) ANTI-SENSE: YES (xi) SEQUENCE DESCRIPTION: SEQ ID NO: 10:

GGTTGAGCAG GTACACATCA G                                 21

(2) INFORMATION FOR SEQ ID NO: 11:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 11:

CAATACTGTG GGCTCCTCC                                       19

(2) INFORMATION FOR SEQ ID NO: 12:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 12:

GCTCAGGTCC ATGACTG                                         17

(2) INFORMATION FOR SEQ ID NO: 13:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 13:

CTCATGAGCA TTGATAG                                         17

(2) INFORMATION FOR SEQ ID NO: 14:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 14:

CTGAGCGCAA CCATACC                                         17

(2) INFORMATION FOR SEQ ID NO: 15:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 15:

GCTAGAAGTC CTTCAGG                                         17

(2) INFORMATION FOR SEQ ID NO: 16:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 16:

```
GGATCATGAT CTTCATG                                              17
```

(2) INFORMATION FOR SEQ ID NO: 17:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 17:

```
AAATGAAACC CCACGGATAT AGCAG                                     25
```

(2) INFORMATION FOR SEQ ID NO: 18:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(iv) ANTI-SENSE: YES (xi) SEQUENCE DESCRIPTION: SEQ ID NO: 18:

```
TCCTACAGAG CATCATGAAG ATC                                       23
```

(2) INFORMATION FOR SEQ ID NO: 19:

(i) SEQUENCE CHARACTERISTICS:
        (A) LENGTH: 1607 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 183..1262

(xi) SEQUENCE DESCRIPTION: SEQ ID NO: 19:

```
CGGGGGTTTT GATCTTCTTC CCCTTCTTTT CTTCCCCTTC TTCTTTCCTT CCTCCCTCCC    60

TCTCTCATTT CCCTTCTCCT TCTCCCTCAG TCTCCACATT CAACATTGAC AAGTCCATT    120

AGAAAAGCAA GCTGCTTCTG GTTGGGCCCA GACCTGCCTT GAGGAGCCTG TAGAGTTAA    180

AA ATG AAC CCC ACG GAT ATA GCA GAT ACC ACC CTC GAT GAA AGC ATA      227
   Met Asn Pro Thr Asp Ile Ala Asp Thr Thr Leu Asp Glu Ser Ile
    1               5                  10                  15

TAC AGC AAT TAC TAT CTG TAT GAA AGT ATC CCC AAG CCT TGC ACC AAA     275
Tyr Ser Asn Tyr Tyr Leu Tyr Glu Ser Ile Pro Lys Pro Cys Thr Lys
```

```
                    20                  25                  30
GAA GGC ATC AAG GCA TTT GGG GAG CTC TTC CTG CCC CCA CTG TAT TCC    323
Glu Gly Ile Lys Ala Phe Gly Glu Leu Phe Leu Pro Pro Leu Tyr Ser
                35                  40                  45

TTG GTT TTT GTA TTT GGT CTG CTT GGA AAT TCT GTG GTG GTT CTG GTC    371
Leu Val Phe Val Phe Gly Leu Leu Gly Asn Ser Val Val Val Leu Val
            50                  55                  60

CTG TTC AAA TAC AAG CGG CTC AGG TCC ATG ACT GAT GTG TAC CTG CTC    419
Leu Phe Lys Tyr Lys Arg Leu Arg Ser Met Thr Asp Val Tyr Leu Leu
        65                  70                  75

AAC CTT GCC ATC TCG GAT CTG CTC TTC GTG TTT TCC CTC CCT TTT TGG    467
Asn Leu Ala Ile Ser Asp Leu Leu Phe Val Phe Ser Leu Pro Phe Trp
    80                  85                  90                  95

GGC TAC TAT GCA GCA GAC CAG TGG GTT TTT GGG CTA GGT CTG TGC AAG    515
Gly Tyr Tyr Ala Ala Asp Gln Trp Val Phe Gly Leu Gly Leu Cys Lys
                100                 105                 110

ATG ATT TCC TGG ATG TAC TTG GTG GGC TTT TAC AGT GGC ATA TTC TTT    563
Met Ile Ser Trp Met Tyr Leu Val Gly Phe Tyr Ser Gly Ile Phe Phe
            115                 120                 125

GTC ATG CTC ATG AGC ATT GAT AGA TAC CTG GCG ATA GTG CAC GCG GTG    611
Val Met Leu Met Ser Ile Asp Arg Tyr Leu Ala Ile Val His Ala Val
        130                 135                 140

TTT TCC TTG AGG GCA AGG ACC TTG ACT TAT GGG GTC ATC ACC AGT TTG    659
Phe Ser Leu Arg Ala Arg Thr Leu Thr Tyr Gly Val Ile Thr Ser Leu
    145                 150                 155

GCT ACA TGG TCA GTG GCT GTG TTC GCC TCC CTT CCT GGC TTT CTG TTC    707
Ala Thr Trp Ser Val Ala Val Phe Ala Ser Leu Pro Gly Phe Leu Phe
160                 165                 170                 175

AGC ACT TGT TAT ACT GAG CGC AAC CAT ACC TAC TGC AAA ACC AAG TAC    755
Ser Thr Cys Tyr Thr Glu Arg Asn His Thr Tyr Cys Lys Thr Lys Tyr
                180                 185                 190

TCT CTC AAC TCC ACG ACG TGG AAG GTT CTC AGC TCC CTG GAA ATC AAC    803
Ser Leu Asn Ser Thr Thr Trp Lys Val Leu Ser Ser Leu Glu Ile Asn
            195                 200                 205

ATT CTC GGA TTG GTG ATC CCC TTA GGG ATC ATG CTG TTT TGC TAC TCC    851
Ile Leu Gly Leu Val Ile Pro Leu Gly Ile Met Leu Phe Cys Tyr Ser
        210                 215                 220

ATG ATC ATC AGG ACC TTG CAG CAT TGT AAA AAT GAG AAG AAG AAC AAG    899
Met Ile Ile Arg Thr Leu Gln His Cys Lys Asn Glu Lys Lys Asn Lys
    225                 230                 235

GCG GTG AAG ATG ATC TTT GCC GTG GTG GTC CTC TTC CTT GGG TTC TGG    947
Ala Val Lys Met Ile Phe Ala Val Val Val Leu Phe Leu Gly Phe Trp
240                 245                 250                 255

ACA CCT TAC AAC ATA GTG CTC TTC CTA GAG ACC CTG GTG GAG CTA GAA    995
Thr Pro Tyr Asn Ile Val Leu Phe Leu Glu Thr Leu Val Glu Leu Glu
                260                 265                 270

GTC CTT CAG GAC TGC ACC TTT GAA AGA TAC TTG GAC TAT GCC ATC CAG   1043
Val Leu Gln Asp Cys Thr Phe Glu Arg Tyr Leu Asp Tyr Ala Ile Gln
            275                 280                 285

GCC ACA GAA ACT CTG GCT TTT GTT CAC TGC TGC CTT AAT CCC ATC ATC   1091
Ala Thr Glu Thr Leu Ala Phe Val His Cys Cys Leu Asn Pro Ile Ile
        290                 295                 300

TAC TTT TTT CTG GGG GAG AAA TTT CGC AAG TAC ATC CTA CAG CTC TTC   1139
Tyr Phe Phe Leu Gly Glu Lys Phe Arg Lys Tyr Ile Leu Gln Leu Phe
    305                 310                 315

AAA ACC TGC AGG GGC CTT TTT GTG CTC TGC CAA TAC TGT GGG CTC CTC   1187
Lys Thr Cys Arg Gly Leu Phe Val Leu Cys Gln Tyr Cys Gly Leu Leu
320                 325                 330                 335

CAA ATT TAC TCT GCT GAC ACC CCC AGC TCA TCT TAC ACG CAG TCC ACC   1235
Gln Ile Tyr Ser Ala Asp Thr Pro Ser Ser Ser Tyr Thr Gln Ser Thr
```

```
Gln Ile Tyr Ser Ala Asp Thr Pro Ser Ser Tyr Thr Gln Ser Thr
                340                 345                 350

ATG GAT CAT GAT CTC CAT GAT GCT CTG TAGAAAAATG AAATGGTGAA                    1282
Met Asp His Asp Leu His Asp Ala Leu
                355                 360

ATGCAGAGTC AATGAACTTT TCCACATTCA GAGCTTACTT TAAAATTGGT ATTTTTAG              1342

AAGAGATCCC TGAGCCAGTG GTCAGGAGGA AAGGCTTACA CCCACAGGTG GGAAAGAC              1402

GTTCTCATCC CTGCAGGNAG GTTTTTCTTC TCCCCACTTA GANAAAGTNC CAGGCCTG              1462

AGGGGTCCAA CCCNGGGTTG AGGATCCTTC CCCCAAACCC AGGGTTTGGC CTGGAGGA              1522

AATNCAAAAN NTTTNTTGAA ACTCTTGAAN ANGTTGNGNT AAGTTTNGGG GGGTTNTT              1582

GAAGGNAAGT TTTTCCCTTC TTNCC                                                  1607

(2) INFORMATION FOR SEQ ID NO: 20:

(i) SEQUENCE CHARACTERISTICS:
        (A) LENGTH: 360 amino acids
        (B) TYPE: amino acid
        (D) TOPOLOGY: linear (ii) MOLECULE TYPE: protein (xi) SEQUENCE DESCRIPTION: SEQ ID NO: 20:

Met Asn Pro Thr Asp Ile Ala Asp Thr Thr Leu Asp Glu Ser Ile Tyr
 1               5                  10                  15

Ser Asn Tyr Tyr Leu Tyr Glu Ser Ile Pro Lys Pro Cys Thr Lys Glu
                20                  25                  30

Gly Ile Lys Ala Phe Gly Glu Leu Phe Leu Pro Pro Leu Tyr Ser Leu
            35                  40                  45

Val Phe Val Phe Gly Leu Leu Gly Asn Ser Val Val Val Leu Val Leu
        50                  55                  60

Phe Lys Tyr Lys Arg Leu Arg Ser Met Thr Asp Val Tyr Leu Leu Asn
 65                  70                  75                  80

Leu Ala Ile Ser Asp Leu Leu Phe Val Phe Ser Leu Pro Phe Trp Gly
                85                  90                  95

Tyr Tyr Ala Ala Asp Gln Trp Val Phe Gly Leu Gly Leu Cys Lys Met
                100                 105                 110

Ile Ser Trp Met Tyr Leu Val Gly Phe Tyr Ser Gly Ile Phe Phe Val
                115                 120                 125

Met Leu Met Ser Ile Asp Arg Tyr Leu Ala Ile Val His Ala Val Phe
            130                 135                 140

Ser Leu Arg Ala Arg Thr Leu Thr Tyr Gly Val Ile Thr Ser Leu Ala
145                 150                 155                 160

Thr Trp Ser Val Ala Val Phe Ala Ser Leu Pro Gly Phe Leu Phe Ser
                165                 170                 175

Thr Cys Tyr Thr Glu Arg Asn His Thr Tyr Cys Lys Thr Lys Tyr Ser
                180                 185                 190

Leu Asn Ser Thr Thr Trp Lys Val Leu Ser Ser Leu Glu Ile Asn Ile
            195                 200                 205

Leu Gly Leu Val Ile Pro Leu Gly Ile Met Leu Phe Cys Tyr Ser Met
        210                 215                 220

Ile Ile Arg Thr Leu Gln His Cys Lys Asn Glu Lys Lys Asn Lys Ala
225                 230                 235                 240

Val Lys Met Ile Phe Ala Val Val Val Leu Phe Leu Gly Phe Trp Thr
                245                 250                 255
```

-continued

```
Pro Tyr Asn Ile Val Leu Phe Leu Glu Thr Leu Val Glu Leu Glu Val
            260                 265                 270

Leu Gln Asp Cys Thr Phe Glu Arg Tyr Leu Asp Tyr Ala Ile Gln Ala
        275                 280                 285

Thr Glu Thr Leu Ala Phe Val His Cys Cys Leu Asn Pro Ile Ile Tyr
    290                 295                 300

Phe Phe Leu Gly Glu Lys Phe Arg Lys Tyr Ile Leu Gln Leu Phe Lys
305                 310                 315                 320

Thr Cys Arg Gly Leu Phe Val Leu Cys Gln Tyr Cys Gly Leu Leu Gln
                325                 330                 335

Ile Tyr Ser Ala Asp Thr Pro Ser Ser Ser Tyr Thr Gln Ser Thr Met
            340                 345                 350

Asp His Asp Leu His Asp Ala Leu
            355                 360
```

CHEMOKINE RECEPTOR ABLE TO BIND TO MCP-1, MIP-1 α AND/OR RANTES AND ITS USES

This application is a division of Application Ser. No. 09/614,256, filed July 12, 2000, now abandoned which is a continuation of Application Ser. No. 08/875,573, filed October 31, 1997, now U.S. Pat. No. 6,150,132, which is a national stage application of PCT/GB96/00143, filed Jan. 24,1996, the entire content of which is hereby incorporated by reference.

The present invention relates to chemokine receptors.

Chemokines are a growing family of chemotactic cytokines, which have been implicated to play a role in the recruitment and activation of cells (Oppenheim, J. J. et al., Ann Rev Immunol., 9 617–48, (1991), Schall, T. J., Cytokine, 3 165–183, (1991)). They are primarily responsible for the activation and recruitment of leukocytes, but not exclusively so. Further analysis of this superfamily of proteins has shown that it can be divided up into two further subfamilies of proteins. These have been termed CXC or α-chemokines, and the CC or β-chemokines based on the spacings of two conserved cysteine residues near to the amino terminus of the proteins.

To date two receptors have been identified for the CC chemokine family. The first, which is receptor primarily for MIP-1α (Macrophage inflammatory polyceptide-1α) and RANTES (Raised on Activation, Normal T-cell derived and Secreted) has been described previously (Gao, J. L. et al., J. Exp. Med., 177 1421–7 (1993), Neote, K. et al., Cell 72 415–25 (1993)). The second CC-chemokine receptor which has been recently described is for MCP-1 (monocyte chemotractant protein-1) Charo I. et al., Proc. Natl. Acad. Sci. USA 91 2752–2756 (1994). More recently, another receptor US28, expressed by the human cytomegalovirus, has been shown to be a receptor for RANTES, MIP-1α, and MCP-1 (Gao, J. L. and Murphy P. M., J. Biol. Chem. 269, 28539–28542 (1994)). All three receptors are of the seven transmembrane alpha helical segment type, and are expressed into the membranes of cells.

However there remains a need to identify hitherto undisclosed chemokine receptors and to characterise them in order to develop a more complete picture of the structure and function of chemokine receptors.

According to the present invention there is provided a chemokine receptor having the amino acid sequence shown in FIG. 3.

This receptor is preferably capable of binding MCP-1, MIS-1α and RANTES. It may be important in basophil and T-cell function.

It can be used to screen or pharmaceutically active agents. The present invention therefore includes within its scope such agents (which may or may not be proteins) They may be provided in a pharmaceutical composition together with a pharmaceutically acceptable carrier.

Such a composition is within the scope of the present invention. It may be prepared by admixing the carrier with the pharmaceutically active agent under sterile conditions. The pharmaceutical composition may be provided in unit dosage form. It may be present as part of a kit including instructions for use.

The pharmaceutical composition may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route.

A receptor of the present invention can be used to screen for agents useful in treating allergies e.g. asthma, atopic dermatitis, rhinitis, hay fever, eczema or food allergies. It may also be useful in screening for agents useful in treating conjunctivitis. MCP-1, MIP-1α and RANTES all bind to the receptor of the present invention and are capable of causing histamine release from basophils. An agent which blocks this binding may thereby prevent or reduce the release of histamine from basophils (i.e. act antagonistically to MCP-1, MIP-1α or RANTES). Such agents may be variants of MCP-1, MIP-1α or RANTES (in which one or more amino acids are deleted, substituted or inserted relative to MCP-1, MIP-1α or RANTES), although this is not essential.

It may also be involved in the activation of T-lymphocytes, a common characteristic of immune and other inflammatory states.

The binding of agents to the receptor of the present invention can be assayed by suitable techniques.

For example, electrophysiological techniques may be used. In one such technique, a Xenopus cocyte, for example, can be used to express a receptor of the present invention. The receptor can be expressed on the oocyte membrane following micro-injection into the oocyte of RNA coding for said receptor.

When a ligand binds to the receptor, it can cause a release of calcium ions either from intracellular stores, or from extracellular sources. These calcium fluxes then cause a chloride current across the cell membrane which can be measured electrophysiologically.

Such currents are discussed in Wahlestedt, C., Ann. N.Y. Acad. Sci. 632 116–22 (1991) and Boton, R et al., J. Physiol. (London) 408 511–534 (1989), for example.

As an alternative to using electrophysiological techniques or other techniques which rely upon a biological response to receptor binding, more direct assays of binding can be used. Thus ligands could be labelled with a detectable label, allowed to bind to a receptor, and the label could then be detected. Suitable labels which could be used include radiolabels, fluorescent labels, enzymes which can cause a detectable change, etc.

The receptor of the present invention may also be used to screen for agents suitable for treating atheromas. In this regard it should be noted that MCP-1 is a key recruiter of monocytes to atherosclerotic plagues. The receptor can be used to screen for agents which prevent or reduce such recruitment (act antagonistically to MCP-1α). Such agents may be variants of MCP-1 itself (wherein one or more amino acids are deleted, substituted or inserted relative to MCP-1), although this is not essential.

A further use of the receptor of the present invention is to screen for agents which cause inhibition of stem cell proliferation, in other words to screen for agonists of MIP-1α. MIP-1α has been shown (Graham, G. J. et al., Nature 344 442-(1990)) to inhibit proliferation of hemopoetic stem cell proliferation. As such, receptor agonists could be used to prevent stem cell proliferation during chemotherapy, which would therefore protect the stem cells from the potentially damaging effects of such chemotherapy.

MIP-1α is known to be a stem cell proliferation inhibitor and agents which are also stem cell proliferation inhibitors can be screened using the receptor of the present invention. Such agents may be variants of MIP-1α itself (wherein one or more amino acids are deleted, substituted or inserted relative to MIP-1α), although this is not essential.

Another use of the receptor of the present invention is in screening for agents useful in reducing the likelihood of transplant rejection or in increasing the length of time before rejection occurs. High levels of RANTES are sometimes found in renal grafts and may be associated with the rejection of such grafts. Agents which prevent or reduce the binding of RANTES to the receptor of the present invention may therefore be useful in transplantation by acting antagonistically to RANTES. Such agents may be variants of RANTES itself (wherein one or more amino acids are deleted, substituted or inserted relative to RANTES), although this is not essential.

A further use of the present invention is in screening for substances useful in treating diseases mediated by viruses. Thus it may be used as a screen for antiviral agents.

One example of this is in screening for agents useful in treating AIDS. MIP-1α and RANTES levels have been suggested as being at least partially responsible for certain AIDS patients surviving longer than others. Since a receptor of the present invention may bind to MIP-1α and/or RANTES, it can be used for screening for other agents which could be useful in treating AIDS.

It is also notable that Human Cytomegalovirus and Herpes viruses have chemokine receptors. The present invention could be used to screen for agents useful in treating diseases mediated by such viruses.

It should be noted that the present invention is not limited to the receptor having the amino acids sequence shown in FIG. 3 but that it covers variants (allelic and non-allelic variants) having one or more amino acid deletions, insertions or substitutions relative to said sequence, provided that said variants are capable of binding to at least one of the chemokines: RANTES, MIP-1α and MCP-1. (Desirably, however, the receptors are capable of binding to all of these chemokines). Binding may be determined by monitoring the response of cells in electrophysiological assay using oocytes, as already described.

For example, it will be appreciated by the skilled person that various amino acids may often be substituted for other amino acids which have similar properties without substantially altering or adversely affecting certain properties of a protein. Thus the amino acids glycine, valine, leucine or isoleucine can often be substituted for one another (amino acids having aliphatic hydroxyl side chains). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains) and cysteine and methionine (amino acids having sulphur containing side chains). Thus the present invention includes within its scope variants of the receptor shown in FIG. 3 which includes one or more such substitutions.

It is however preferred that variants of the receptor having the amino acid sequence shown in FIG. 3 have substantial amino acid identity with said amino acid sequence. The degree of amino acid identity can be calculated using a program such as "bestfit" (Smith and Waterman, Advances in Applied Mathematics, 482–489 (1981)) to find the best segment of similarity between the two sequences. The alignment is based on maximising the score achieved using a matrix of amino acid similarities, such as that described by Schwarz and Dayhof (1979) Atlas of Protein Sequence and Structure, Dayhof, M. O., Ed pp 353–358.

Preferably however the degree of sequence identity is at least 50% or at least 60%, and more preferably it is above 75%. Sequence identities of at least 80%, e.g. at least 90% or at least 95%, are most preferred.

The receptor or variant thereof may include an N-terminal methionine. Such methionines are sometimes incorporated during translation and not subsequently removed.

The receptor or variant may be covalently linked to another moiety (e.g. a protein). Thus fusion proteins may be formed. These are well known in the art and may be used to assist in identification or purification or to otherwise alter the properties of the receptor of a variant thereof (e.g. to alter its stability and/or is binding properties).

Truncated variants of the receptor having the amino acid sequence shown in FIG. 3 may also be provided since one or more amino acids may be deleted from said sequence, whilst retaining binding to MIP-1α, RANTES and/or MCP-1. These may be N-terminal deletions, C-terminal deletions or may occur within said sequence.

The receptor or variant (of whatever nature) may be provided in substantially pure form. It may be isolated from other proteins and may be isolated from a cell membrane. It may be in glycosylated or unglycosylated form (depending upon the expression system used). A receptor or variant thereof of the present invention may be provided by any appropriate technique.

Gene cloning techniques are preferably used. Such techniques are disclosed, for example, in J. Sambrook et al., *Molecular Cloning* 2nd Edition, Cold Spring Harbor Laboratory Press (1989).

Alternatively, chemical synthesis may be used (although this is less preferred). For example, short synthetic peptides may be prepared and then linked together to provide a substance of the present invention. Such peptides can be prepared by techniques known to those skilled in the art. Thus one end of a molecule can be immobilised and desired amino acid residue can be added sequentially. Protective groups can be used to avoid undesired side-reactions and may then be removed.

Variants of the receptor of the present invention together with the receptor itself are referred to below as substances of the present invention.

Such substances can be used in raising or selecting antibodies. The present invention therefore includes antibodies which bind to a substance of the present invention. Preferred antibodies bind specifically to substances of the present invention so that they can be used to purify such substances. The antibodies may be monoclonal or polyclonal.

Polyclonal antibodies can be raised by stimulating their production in a suitable animal host (e.g. a mouse, rat, guinea pig, rabbit, sheep, goat or monkey) when the substance of the present invention is injected into the animal. If necessary an adjuvant may be administered together with the substance of the present invention. The antibodies can then be purified by virtue of their binding to a substance of the present invention.

Monoclonal antibodies can be produced from hybridomas. These can be formed by fusing myeloma cells and spleen cells which produce the desired antibody in order to form an immortal cell line. This is the well known Kohler & Milstein technique (*Nature* 256 52–55 (1975))

Techniques for producing monoclonal and polyclonal antibodies which bind to a particular protein are now well developed in the art. They are discussed in standard immunology textbooks, for example in Roitt et al, *Immunology* second edition (1989), Churchill Livingstone, London.

In addition to whole antibodies, the present invention includes derivatives thereof which are capable of binding to substances of the present invention.

Thus the present invention includes antibody fragments and synthetic constructs. Examples of antibody fragments and synthetic constructs are given by Dougall et al in *Tibtech* 12 372–379 (September 1994).

Antibody fragments include, for example, Fab, F(ab')$_2$ and Fv fragments (see Roitt et al [supra]).

Fv fragments can be modified to produce a synthetic construct known as a single chain Fv (scFv) molecule. This includes a peptide linker covalently joining V$_h$ and V$_1$ regions which contribute to the stability of the molecule.

Other synthetic constructs include CDR peptides. These are synthetic peptides comprising antigen binding determinants. Peptide mimetics may also be used. These molecules are usually conformationally restricted organic rings which mimic the structure of a CDR loop and which include antigen-interactive side chains.

Synthetic constructs include chimaeric molecules. Thus, for example, humanised (or primatised) antibodies or derivatives thereof are within the scope of the present invention. An example of a humanised antibody is an antibody having human framework regions, but rodent hypervariable regions.

Synthetic constructs also include molecules comprising a covalently linked moiety which provides the molecule with some desirable property in addition to antigen binding. For example the moiety may be a label (e.g. a fluorescent or radioactive label) or a pharmaceutically active agent.

The antibodies or derivatives thereof of the present invention have a wide variety of uses. They can be used in purification and/or identification of the substances of the present invention. Thus they may be used in diagnosis.

They can be provided in the form of a kit for screening for the substances of the present invention.

The present invention also includes within its scope nucleic acid molecules coding for substances of the present invention (i.e. for the aforesaid receptor or variants thereof). The nucleic acid molecules may be RNA or DNA and may be provided in isolated or recombinant form.

Nucleic acid molecules of the present invention may be provided by any appropriate technique.

Gene cloning techniques are preferred (see Sambrook et al, supra). Variants of a given nucleic acid sequence can be prepared by mutagenesis techniques (e.g. site directed mutagenesis).

Chemical synthesis techniques can alternatively be used, but are less preferred.

Vectors may be used to incorporate the nucleic acid molecules of the present invention. The vectors may be eukaryotic or prokaryotic vectors and may be incorporated into appropriate host cells or into non-cellular expression systems.

Nucleic acid molecules which are complementary to the aforesaid nucleic acid molecules are also within the scope of the present invention. These are sometimes referred to as "antisense molecules". They can hybridise to complementary nucleic acid molecules and may thereby prevent or reduce the expression of a gene product. Thus they can be used to alter gene expression.

The use of such molecules is useful in studying gene function and regulation. Appropriate labelling and hybridisation techniques can be useful to identify the location of coding regions.

The present invention also includes within its scope nucleic acids which can be used as probes for chemokine receptors. Preferred probes can hybridise specifically to a nucleic acid coding for the protein having the amino acid sequences given in FIG. 3, or for variants thereof, as described above. Such probes can be of any suitable length, but would typically be above 15 nucleotides long and may be at least 100 nucleotides long.

Desirably probes will hybridise to a target sequence under stringent hybridisation conditions. An example of stringent hybridisation conditions is a temperature of 35°–65° C. and a salt concentration of about 0.9 molar. Other stringent hybridisation conditions may be used and the salt concentration need not be as high as 0.9 molar.

The nucleic acid sequences given in FIGS. 1 and 3 herein or fragments thereof can be used as probes or primers or to prepare probes or primers.

The primers may be used to amplify nucleic acid sequences e.g. by using PCR or other amplification techniques. The probes may be used in diagnosis or in purification.

The present invention will now be explained by way of example only, with reference to the accompanying drawings, wherein:

FIG. 1 shows a cDNA sequence and a deduced amino acid sequence of a clone designated "TM(2-7)5.5", which was used to probe a human spleen λGT11 cDNA library.

FIG. 2 shows various primers (SEQ ID NOS:7–18) which were used in sequencing a clone isolated from the library referred to in respect of FIG. 1 above by using the TM(2-7)5.5 DNA as a probe.

FIGS. 3A–B shows the cDNA sequence and the deduced amino acid sequence in respect of the clone referred to in respect of FIG. 2 above, the clone being designated "K5.5".

FIGS. 4 to 6 show Northern Blot analyses prepared using TM(2-7)5.5 DNA in various hybridisation studies. In these figures the following scoring system is used:

+++ Very strong positive signal visible after four hours' exposure of the autoradiograph.

++ Clear positive signal visible after four hours' exposure of the autoradiograph.

+ Signal not visible after four hours' exposure of the autoradiograph, but clear after 24 hours.

+/− Weak positive signal only visible after 24 hours' exposure.

− No signal.

Probes were used at a specific activity of $10^6$ cpm/ml hybridisation solution.

FIG. 7 shows on agarose gels an analysis of K5.5 receptor mRNA expression products from leukocytes and some human cell lines, RNA having been amplified using reverse transcriptase PCR.

Figure 8A:
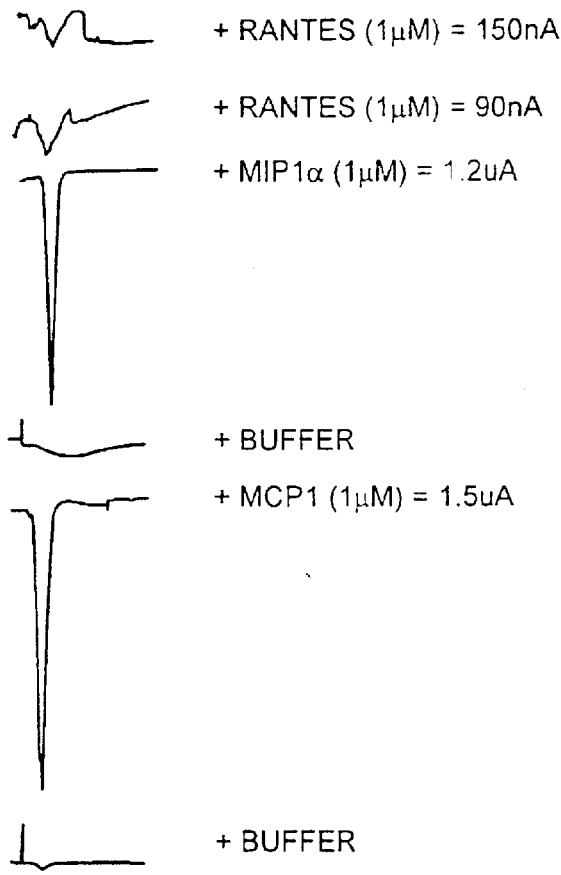

FIG. 8A shows an analysis of the current induced in voltage clamped Xenopus oocytes, into which K5.5 cRNA had been micro-injected, on stimulation with various chemokine ligands.

Figure 8B:
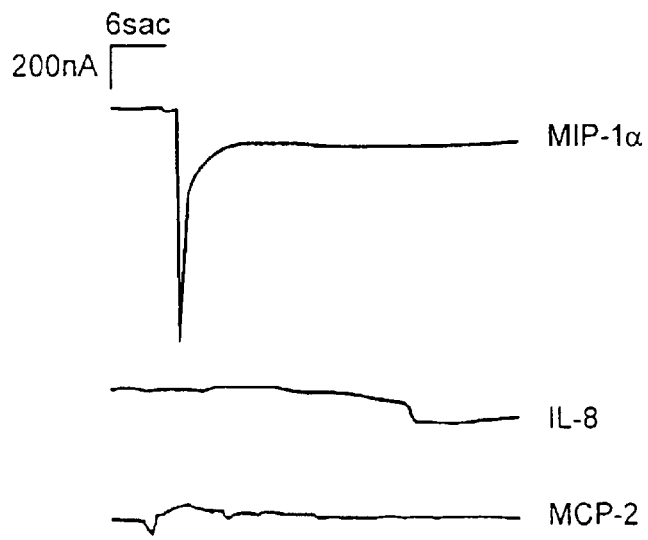

FIG. 8B shows an analysis similar to that performed in respect of FIG. 8A but using different chemokines (apart from MIP-1α, which is shown in both figures for comparison). The present inventors were unable to obtain any data showing that IL-8 binds to CC-CKR3 molecules. Preferred receptors within the scope of the present invention do not bind to IL-8.

Figure 9:
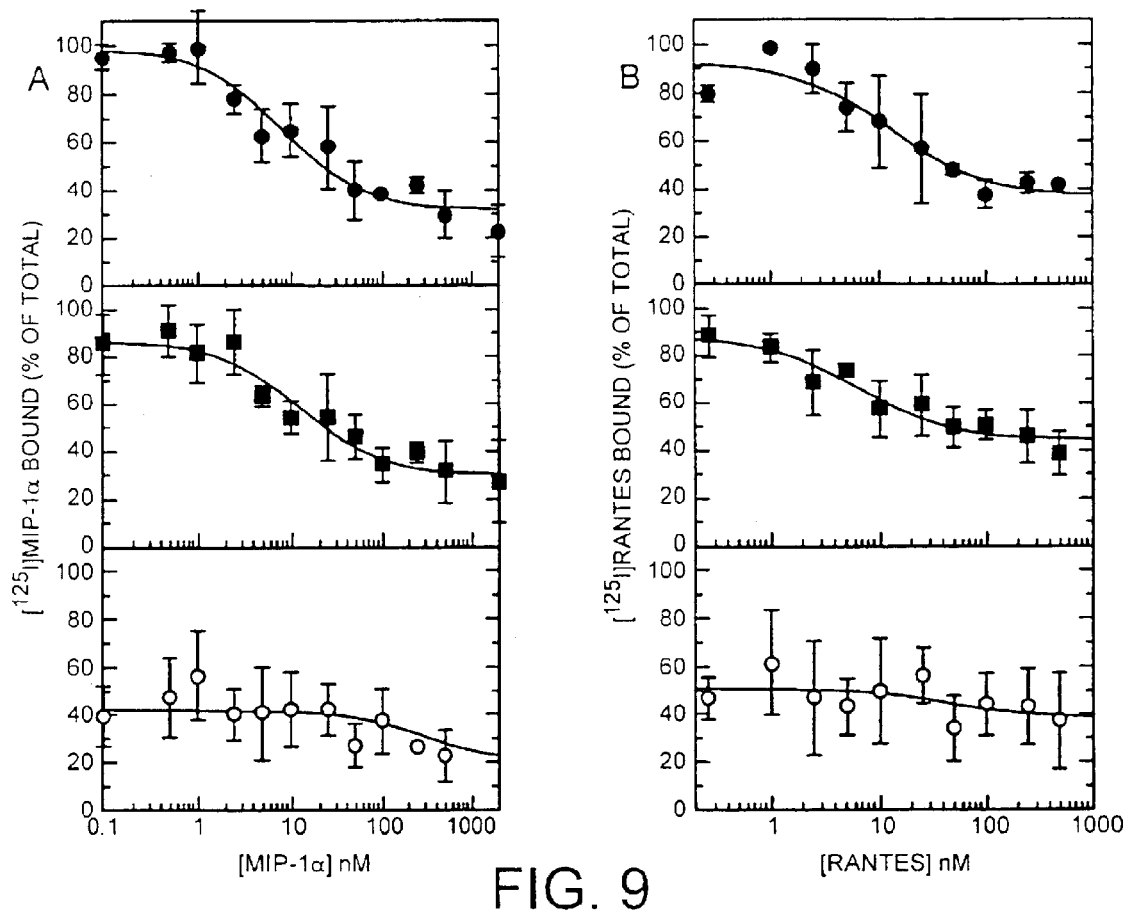

FIG. 9 shows the results of a binding assay using [$^{125}$I] MIP-1α and [$^{125}$I] RANTES to bind to human and murine CC-CKR-3 molecules.

EXAMPLES

An alignment of the amino acid sequences of IL-8 receptor A and B and of the C—C CKR-1 (MIP-1α/RANTES receptor) indicated that a region between proposed transmembrane domains 3 and 4 contains the conserved amino add sequence R Y L A I V H A (SEQ ID NO:1).

A second conserved amino acid sequence occurs in the proposed 7th transmembrane domain in these three receptors as well as in two non-chemokine chemotactic peptide receptors for fMLP (formyl-methionine-leucine-phenylalanine) and C5a as follows (SEQ ID NO:2):
C L(or V,I) N P I(or L,M,V) I(or L) Y A(or V) F(or V)

Degenerate oligonucleotides were prepared containing the majority of possible codons which could be translated to give the above-mentioned amino acid sequences.

These oligonucleotides had the sequences (SEQ ID NOS:3 and 4):
a) sense 5' GIT AYY TIG CIA THG TIC AYG C
or
b) antisense 5' AMI RCR TAI ADI AII GGR TTI AIR C
using the IUB/GCG codes, wherein I=inosine which can substitute for A, T, G, or C
Y=C or T
H=A, C or T
M=A or C
R=A or G
D=A, G or T The oligonucleotides were then used to clone a human CC chemokine receptor using the procedure set out below.
(a) Cloning of a Sequence Designated Human K5.5 (CC-CKR-3)* p(* The designation CC-CKR-3 is used here for consistency with the designation used in the priority document. However it is noted that other research groups are now using the designation CC-CKR-3 for a different molecule and that the molecule referred to herein as CC-CKR-3 may now be referred to in the literature as CC-CKR-4.)

Total RNA was isolated from $1 \times 10^8$ KU812 cells by the method of Chomczynski and Sacchi, (1987) (Single-step method of RNA isolation by acid guanidinium thiocyanate-phenol-chloroform extraction, Anal. Biochem. 162 156–159). These cells were from a human basophilic KU812 cell line which was a gift of Dr K Kishi, Niigata, Japan.

PolyA+ mRNA was subsequently isolated by oligodT cellulose chromatography using a polyA quik mRNA purification kit (Stratagene). Single-stranded cDNA was prepared from 1 µg of polyA+ mRNA in a 50 µl reaction containing 1 µg oligodT$_{12-18}$, 4 mM methyl mercuric hydroxide, 1 mM dNTPs, 50mM Tris-HCl pH 8.3 buffer, 50 mM KCl, 8 mM MgCl$_2$, 10 units RNAsin and 100 units of AMV reverse transcriptase-XL (Life Sciences Inc.) for 60 mm at 42° C. 5 µl aliquots of the reaction mixture were then subjected to 40 cycles of POR (95° C., 2 mm; 37° C., 2 mm and 72° C., 2 mm) in 10 mM Tris-HCl pH 8.3 buffer, 50 mM KCl, 1.5 mM MgCl$_2$, 0.2 mM dNTPS and 2.5 units of AmplitaqTM (Perkin Elmer Cetus) using 3 µM of each degenerate oligonucleotide primer (sense 5' GIT AYY TIG CIA THG TIC AYG C, SEQ ID NO:3 and antisense 5' AMI RCR TAI ADI AII GGR TTI AIR C, SEQ ID NO:4) in a Techne PHC-2 thermal cycler.

PCR reaction products were visualized on 1% agarose gels containing 0.5 µg/ml ethidium bromide. Reaction products migrating at the predicted size (500–550 bp) were gel purified by standard methods (Sambrook J. et al., 1989 in Molecular Cloning: A Laboratory Manual. Cold Spring Harbor Laboratory Press. Cold Spring Harbor, N.Y.). Gel purified DNA was then rendered blunt-ended by sequential treatment with T4 polynucleotide kinase (New England Biolabs) according to the manufacturer's instructions, in a total volume of 50 µl for 1 h at 37° C. After this time, 2.5 µl of 2.5 EM dNTPs and 1 µl of E. coli DNA polymerase I Klenow fragment (New England Biolabs) were added and the incubation continued for a further 30 min at 37° C. The reaction mixture was then heat inactivated at 70° C. for 30 min and then extracted once with Tris-HCl pH 8.0 saturated phenol/chloroform (1:1 v/v). DNA was precipitated by addition of 10 µl 3M sodium acetate pH 5.5, 1 µl glycogen (20 mg/ml) (Boehringer) and 250 µl ethanol at −20° C. The DNA was recovered by centrifugation at 10 000×g for 20 min at 4° C. and washed with 70% ethanol. The final pellet was resuspended in sterile water at a concentration of 10 ng/µl.

A pBluescript II SK-cloning vector (Stratagene) was prepared as follows: 20 µg of CsCl gradient purified plasmid was digested in a reaction volume of 100 µl for 2 h at 37° C. with 200 units of Eco RV or Eco RI (New England Biolabs) according to the manufacturer's instructions. After 2 h, the digested vector was treated with 10 µl of calf intestinal alkaline phosphatase (20 units/ml) (Boehringer) for a further 30 min at 37° C. The reaction mixture was inactivated by heating at 68° C. for 15 min and then extracted once with Tris-HCl pH 8.0 saturated phenol/chloroform (1:1 v/v). Plasmid DNA was precipitated by addition of 10 µl 3M sodium acetate pH 5.5 and 250 µl ethanol at −20° C. The DNA was recovered by centrifugation at 10 000× g for 20 min at 4° C., washed with 70% ethanol. The final pellet was resuspended in sterile water at a concentration of 50 ng/ml.

Blunt-ended PCR product (10 ng) was ligated to 50 ng of Eco RV digested, alkaline phosphatase treated pBluescript II SK-plasmid cloning vector in a 20 µl volume using 2 µl of T4 DNA ligase (400 000 units/ml) (New England Biolabs) for at least 16 h at 15° C. Ligation products were diluted to 100 µl with 1× TE (10 mM Tris-HCl pH 8.0/1 mM EDTA) and phenol/chloroform extracted as described previously. Ligation products were precipitated by the addition of 10 µl 3M sodium acetate pH 5.5, 1 µl glycogen (20 mg/ml) and 250 µl ethanol for 15 min at −70° C. DNA was recovered by centrifugation as described above and resuspended in 10 µl of sterile water. Five µl of resuspended ligation products were then electroporated into electrocompetent E. coli strain XL-1 blue (recA1, endA$_1$, gyrA96, thi-1, hsdR17, supE44, relA1, lac, {F' proAB, lacIqZDM15, Tn10 (tet$^r$)] (40 µl) using a Bio Rad Gene pulser according to the manufacturer's instructions. Following electroporation, 1 ml of LB medium was added and cells were grown at 37° C. for 1 h. After this time, 100 µl aliquots of the culture medium were plated on LB plates containing 100 µg/ml of ampicillin and grown up for 16 h at 37° C. Individual bacterial colonies were then picked into 5 ml of LB medium containing 100 µg/ml of ampicillin and grown overnight at 37° C. Small scale plasmid DNA preparations (mini-preps) were then made from 3 ml of each culture using a Wizard™ mini-prep DNA purification system (Promega) according to the manufacturer's instructions. Three µl aliquots of mini-prep DNA was then digested with restriction enzymes Hind III and Eco RI (both from New England Biolabs) according to the manufacturers instructions in a reaction volume of 15 µl. Reaction products were analysed on 1% agarose gels containing 0.5 µg/ml ethidium bromide. Mini-prep DNAs which yielded an insert size of approximately 500–550 bp were then subjected to DNA sequence analysis using T3 and T7 primers and Sequenase (USB) according to the manufacturer's instructions.

A comparison of the sequences obtained against the Genank/EMEL/DDBJ databases revealed that 10/23 sequences analysed showed 60% identity at the DNA level to the human C—C CKR-1 (MIP-1α/RPNTES receptor) (Neote et al., Molecular cloning, functional expression and signalling characteristics of a C—C chemokine receptor, Cell 72 415–425 (1993)). The sequence of one of the clones designated TM(2-7)5.5 (shortened to K5.5) is shown in FIG. 1.

CsCl gradient-purified plasmid DNA was prepared for clone K5.5 by standard methods. 20 μg of plasmid DNA was digested at 37° C. with restriction enzymes Hind III and Eco RI according to the manufacturer's instructions (New England Biolabs). Digestion products were analysed on 1% agarose gels containing 0.5 μg/ml ethidium bromide. The 514 bp insert DNA corresponding to the sequenced PCR product was gel purified as described previously. One hundred ng of the 514 bp insert was labelled with $^{32}$P-dCTP (Amersham International) using a random-primed DNA-labelling kit (Boehringer) according to the manufacturer's instructions, and used to screen $5 \times 10^5$ clones of a human spleen λGT11 cDNA library (Clontech) according to the manufacturer's instructions. Following hybridization, duplicating positives were rescreened with the same probe until a pure positive phage plaque was obtained. Phage DNA was recovered from positive plaques using standard methods (Sambrook J. et al (1989)). Purified phage DNA (100 μg) was digested with 200 units of Eco RI (New England Bolabs) in buffer 2 (New England Biolabs) for 16 h at 37° C. Digestion products were fractionated on 1% agarose gels containing ethidium bromide (0.5 g/ml) and cDNA inserts were gel purified and ligated into the Eco RI site of pBluescript II SK-vector as described above. Ligation products were transformed into E. coli strain XL-1 blue (recA1, endA1, gyrA96, thi-1, hsdR17, supE44, relA1, lac, {F' proAB, lacIqZDM15, Tn10 (tet$^r$)] by electroporation as previously. Individual, ampicillin resistant bacterial colonies were inoculated into L-Broth containing 100 μg/ml ampicillin and grown up for 16 h at 37° C. Mini-prep DNA was prepared from 3 ml of overnight culture medium as described above. Three μl aliquots of min-prep DITA was then digested with restriction enzyme Eco RI according to the manufacturers' instructions in a reaction volume of 15 μl. Reaction products were analysed on it agarose gels containing 0.5 μg/ml ethidium bromide. Mini-preps which contained cDNA inserts were subsequently sequenced using Sequenase™ and T3 and T7 primers on an Applied Biosystems DNA sequencer.

One clone designated E1-C19, was shown by sequencing with the T7 primer to contain the putative 5' end of K5.5. CsCl gradient-purified DNA of clone E1-C19 was subsequently resequenced with T3 and T7 primers and several internal sequencing primers based on the previous sequencing results (primer sequences are shown in FIG. 2). The sequence of E1-C19 insert cDNA is shown in FIGS. 3A–B.

(b) Northern Blot Analysis

Multiple tissue Northern blots were purchased from Clontech and hybridized to the 514 bp Hind III/Eco RI fragment of pTM(2-7)5.5 according to the manufacturer's instructions. For other Northern blots, total RNA was prepared from cell lines and peripheral blood leukocyte populations by the method of Chomczynski and Sacchi (1987). All of the cell lines used in this study were maintained in RPMI 1640 medium containing 10% heat inactivated FCS and 50 μg/ml gentamycin (all purchased from Gibco-BRL). Total peripheral blood mononuclear cells and polymorphonuclear cells were puriried by density gradient centrifugation on Ficoll (Pharmacia) Leukocytes were sorted by FACS using the appropriately labelled antibody on a FACS star (Becton Dickinson) to obtain pure populations (>90%) of B cells (CD20), T cells (CD4, CD8, CD45R0, CD45RA) and monocytes (CD14). Pulmonary macrophages and mixed lung leukocytes were prepared from resected human lung samples using the method of Nicod et al (1989) (Separation of potent and poorly functional human lung accessory cells based on autofluorescence. J. Leukocyte. Biol. 45 458).

5 μg of each RNA was electrophoresed in 1% agarose gels containing 2.2% (v/v) formaldehyde, transferred to nitrocellulose and probed with the $^{32}$P-dCTP labelled 514 bp insert from TM(2-7)5.5 using standard Northern blot procedure (Sambrook et al (1989)). The results are shown in FIGS. 4 to 6.

(c) Analysis of K5.5 Receptor mRNA Expression in Leukocytes and Some Human Cell Lines by Reverse Transcriptase PCR 10 μg of total RNA (in a volume of 10 μl) and 0.5 μl of 0.5 mg/ml solution of oligodT$_{15}$ were heated at 70° C. for 10 min and then cooled on ice for 2 min, followed by addition of 4 μl of 5× 1st strand buffer, 2 μl of 0.1 M DTT, 1 μl of 10 mmM dNTPs and 1 μl Superscrirt™ for 1 h at 37° C. All reagents for the reverse transcription (RT) reaction were from Gibco-BRL except oligodT$_{15}$ (Stratagene). Two μl aliquots of each RT reaction was then subjected to 40 cycles of PCR (2 min 95° C.; 2 min, 55° C. and 2 min, 72° C.) in a 100 μl reaction mixture containing 100 pmoles each of primers K5-5FLA and K5-5FLB. PCR reaction products (10 μl) were analysed on 1% agarose gels as described above, for the presence of a 1085 bp reaction product corresponding to the full coding sequence of K5.5. The results are shown in FIG. 7, wherein the samples in the lanes indicated in FIG. 7 are as follows:

| Lane | Sample |
|------|--------|
| 1 | Molecular weight markers (1 kb ladder) |
| 2 | PB T cells (IL-2 stimulated) |
| 3 | PB T cells |
| 4 | Jurkat |
| 5 | MOLT-4 |
| 6 | PB B cells |
| 7 | PB B cells |
| 8 | pulmonary macrophages |
| 9 | PB monocytes |
| 10 | KU812 |
| 11 | EOL-3 |
| 12 | SW900 (lung epithelial cell line) |
| 13 | CCLu32 (lung fibroblast cell line) |
| 14 | LL24 (lung fibroblast cell line) |
| 15 | AALT.16 (aortic smooth muscle cell line) |

(d) Expression of K5.5 cRNA in Xenopus Oocytes

CsCl-gradient purified pE1-C19 plasmid DNA (5 μg) was linearized using restriction enzyme Bam HI (New England Biolabs) in a 100 μl reaction volume overnight at 37° C. Linearized plasmids were treated with 2 μl of proteinase K (16.7 mg/ml Boehringer) for 30 min at 37° C. DNA was extracted twice with phenol (0.1 M Tris-saturated pH 8.0) and once with chloroform. Glycogen (1 μl of 20 mg/ml stock solution) was added to the aqueous phase and linearized DNA was precipitated following addition of 0.1 volume of 3 M sodium acetate pH 5.5 and 2.5 volumes of ethanol for 1 h at −80° C. The DNA was recovered by centrifugation (14 000 rpm, 4° C. in a microfuge), washed with 70% ethanol and dissolved in RNase free water at 250 ng/ml.

Capped cRNA transcripts were generated from 1 μg of Ban HI (New England Biolabs) linearized DNA in a 100 μl reaction volume containing 20 μl transcription buffer (5×), 4 μl NTP mix (10 mM ATP, UTP and CTP, 3 mM GTP), 4 μl 0.75M DTT, 2.5 μl RNAsin, 0.5 μl GTP (10 mM), 4 μl CAD analog (10 mum m7G(5')ppp(5')G) and 2.5 μl of T7 or T3 RNA polymerase respectively. All reagents used for the in vitro transcription reaction were from Promega except CAP analog (Pharmacia). After 1.5 h at 37° C., 4 µl RQ1 DNase (Promega) was added and the reaction mixture was incubated for a further 15 min at 37° C. The reaction mixture was extracted twice with 0.1 M Tris-HCl pH 8.0 saturated phenol/chloroform (1:1 v/v) and once with chloroform. Glycogen (1 µl as above) was added to the aqueous phase and cRNA was precipitated overnight at −20° C. after addition of 0.1 volume, 3 M sodium acetate pH 5.5 and 2.5 volumes ethanol. cRNA was recovered by centrifugation (14 000 rpm, 4° C., 20 min in a m-croruge), the pellet washed in 70% ethanol and resuspended in sterile water at 1 µg/µl. An approximate estimate of the cRNA concentration was obtained by running an aliquot of the resuspended material on a 1% agarose gel containing 2.2% (v/v) formaldehyde against RNA markers of known concentration. Samples were stored at −80° C. before use.

Oocytes were harvested from adult female Xenopus laevis, by standard methods (Bertrand et al., 1991). Oocytes were defollicullated by incubation in 0.2% (w/v) collagenase (Sigma) in 50 ml OR2 medium without Ca2+ and without Mg2+ in a spinner flask under slow agitation for 2 h at room temperature (OR2 medium is 82.5 mM NaCl, 2.5 mM KCl, 1 mM $Na_2HPO_4$, 15 mM HEPES, 2 mM $CaCl_2$, 1 mM $Mgcl_2$ pH 7.6). Oocytes were rinsed carefully with OR2 followed by MBS (modified Barth's saline: 88 mM NaCl, 1 mM KCl, 0.33 mM $Ca(NO_3)_2$, 0.41 mM $CaCl_2$, 0.82 mM $MgSO_4$, 2.4 mM $NaHCO_3$, 10 mM HEPES, pH 7.6) and allowed to recover for at least 1–2 h in MBS before selecting stage V-VI oocytes. Selected oocytes were incubated in MBS supplemented penicillin/streptomycin (100 units/ml) (Gibco-BRL) overnight at 18° C. before injection.

Oocytes were microinjected using an Inject + Matic air pump (Gabay) using needles made from Drummond calibrated 6 ml capillaries. cRNA (25 ng in 50 nl) was injected into the cytoplasm. Oocytes were individually transferred to wells of a 96 well flat bottom culture dish and incubated in MBS for 24–72 h.

Electrophysiological recordings were made 1–3 days after injection in oocytes superfused with OR2 medium at room temperature under voltage clamped conditions using two microelectrodes (1–2 MΩ, both filled with 3 M KCl), the membrane potential being routinely clamped at −100 mV using a Gene Clamp 500 instrument (Axon).

Test chemokines were purchased from PeptroTech or produced in-house at the Glaxo Institute for Molecular Biology and resuspended at a concentration of 1 µM in PBS. Fifty µl of each chemokine was applied directly onto voltage clamped oocytes and the current induced was monitored on a Tektronix 5113 dual-beam storage oscilloscope linked to an IBM-PC. Where multiple chemokines were tested on a single oocyte, a recovery time of 2 min was allowed between each application. The results are shown in FIG. 8A.

FIG. 8B shows the results of a similar analysis to that illustrated in FIG. 8A, but using different chemokines (apart from MIP-1α).

It can be seen that no significant electrophysiological response was seen when using IL-8, in contrast with the result obtained for MIP-1α.

(e) EL-60 Cell Transfection and Ligand Binding Assay

Thirty µg human CC-CKR-3-pcDNA1neo, murine CC-CKR-3-pcDNA1neo, or pcDNA1neo were electroporated into 500 µl HL-60 cells ($2×10^7$ cells/ml in 0.15 M NaCl, 20 mM HEPES, pH 7.3) using a Bio Rad Geno Pulster (260 volts, 960 µF, 0.4 cm gap cuvette). Cells were seeded into T-175 flasks containing 25 ml AIM-V serum-free media (GIBCO). On day 2 or 3 following transfection the cells were diluted in a total volume of 45 ml AIM-V media containing 600 µg/ml G418, and on day 6, cells were further diluted to 180 ml AIM-V media containing 600 µg/ml G418. On days 7–15 post-transfection cells were maintained in AIM-V media (+G418) at a density of $0.4$–$1.2×10^6$ cells/ml, and binding assays were performed during this time. Equilibrium competition binding was carried out by incubating $5×10_5$ cells in 100 µl binding buffer (1 mM CaCl2, 5 mM $MgCl_2$, 0.5% BSA, 50 mM HEPES, pH 7.2), 0.34 nM [$^{125}$I] radioligand, and 0.5–2000 nM cold ligand in Millipore®-DV96-well filter plates. After 1.5 h incubation at room temperature, cells were washed four times by vacuum filtration with binding buffer containing 0.5 M NaCl. Fifty µl Optiphase scintillant (Wallac) were added to each well, and the radioactivity was measured with a Wallac Microbeta Plate Reader. All binding data was normalized as the percentage of total binding. Total binding for a given ligand was defined as the radioactivity bound in the absence of competing ligand to $5×10^5$ cells transfected with human CC-CKR-3 (range: 1000–2500 cpm).

The results are shown in FIG. 9 which illustrates high affinity binding of [$^{125}$I]MIP-1α and [$^{125}$I] RANTES to human and murine CC-CKR-3. HL-60 cells were transfected with human CC-CKR-3 (●), murine CC-CKR-3 (■), or an empty vector (○) and maintained in AIM-V media containing G418 for 7–15 days. Equilibrium competition assays were performed as described above with [$^{125}$I]MIP-1α (A) and [$^{125}$I]RANTES (B). Each point represents the mean ± S.D. of duplicate points from four (A) or three (B) separate experiments. Data were curve-fitted with GraFit 3.01 software (Leatherbarrow., R. J., GraFit Versions 3.01, Erithicus Softward Ltd., Staines, UK (1992)) using the equation $B/Bmax^{app}=1/(1+([L[/IC_{50}))$, where B=cpm bound, $Bmax^{app}$=cpm bound in the absence of competing ligand, L=competing ligand, and the $IC_{50}$=[radioligand]+$K_d$ (Cheng., Y. and Prusoff., W. H. *Biochem Pharmacol* 22: 3099–3108 (1973)).

What is claimed is:

1. A method of screening for a pharmaceutical agent which affects the activity of a polypeptide comprising the amino acid sequence shown in SEQ ID NO:20 (FIG. 3), comprising:
   (a) contacting one or more pharmaceutical agents with a polypeptide having the amino acid sequence as shown in SEQ ID NO:20 (FIG. 3);
   (b) assaying whether the one or more agents affects polypeptide activity; and
   (c) identifying those pharmaceutical agents which increase or decrease activity of said polypeptide in said screening method.

2. Method of screening according to claim 1 wherein said agent is useful in treating allergies.

3. Method of screening according to claim 1 wherein said agent is useful in treating asthma, hay fever, atopic dermatitis or rhinitis.

4. Method of screening according to claim 1 wherein said agent is useful in treating asthma.

5. Method of screening according to claim 4 wherein said agent is an antagonist.

6. Method of screening according to claim 1 wherein said agent is useful in treating immune and/or inflammatory states associated with T-lymphocyte activation.

7. Method of screening according to claim 1 wherein said agent is useful in reducing the likelihood of transplant rejection or in increasing the length of time before rejection occurs.

8. Method of screening according to claim 1 wherein said agent is useful in treating atheromas.

9. Method of screening according to claim 1 wherein said agent inhibits stem cell proliferation.

10. Method of screening according to claim 1 wherein said agent is useful in the treatment of virus mediated diseases.

11. Method of screening according to claim 1 wherein said agent blocks the binding of MCP-1α and/or RANTES to said polypeptide.

12. Method of screening according to claim 1 wherein said pharmaceutical agent is an antibody.

13. Method of screening according to claim 1 wherein said pharmaceutical agent is a monoclonal antibody.

14. Method of screening according to claim 1 wherein said pharmaceutical agent is a humanized monoclonal antibody.

15. Method of screening according to claim 1 wherein said pharmaceutical agent is an antibody fragment selected from the group consisting of Fab, F(ab')$_2$ and Fv fragments.

16. Method of screening according to claim 1 wherein said pharmaceutical agent is a monoclonal antibody or a fragment thereof useful in treating an immune and/or inflammatory condition associated with T-lymphocyte activation.

* * * * *